US009033008B2

(12) United States Patent
Latos

(10) Patent No.: US 9,033,008 B2
(45) Date of Patent: May 19, 2015

(54) METHOD FOR OPTIMIZING LUMBER DERIVED FROM A LOG

(75) Inventor: Philip Latos, St. Albert (CA)

(73) Assignee: Weyerhaeuser NR Company, Federal Way, WA (US)

( * ) Notice: Subject to any disclaimer, the term of this patent is extended or adjusted under 35 U.S.C. 154(b) by 986 days.

(21) Appl. No.: 13/053,011

(22) Filed: Mar. 21, 2011

(65) Prior Publication Data
US 2011/0168296 A1 Jul. 14, 2011

Related U.S. Application Data

(62) Division of application No. 11/379,515, filed on Apr. 20, 2006, now Pat. No. 7,938,156.

(51) Int. Cl.
B27G 1/00 (2006.01)
A01G 27/00 (2006.01)
G01N 33/46 (2006.01)

(52) U.S. Cl.
CPC *B27G 1/00* (2013.01); *A01G 27/00* (2013.01); *G01N 33/46* (2013.01)

(58) Field of Classification Search
CPC .......................................................... B27G 1/00
USPC ......... 144/340, 359, 360, 367, 369, 370, 373, 144/387, 392, 393; 83/75.5
See application file for complete search history.

(56) References Cited

U.S. PATENT DOCUMENTS

| 3,750,727 | A | * | 8/1973 | Ord ................................. 144/378 |
| 3,931,501 | A | | 1/1976 | Barr et al. |
| 4,082,129 | A | | 4/1978 | Morelock |
| 4,185,672 | A | | 1/1980 | Vit et al. |
| 4,221,974 | A | | 9/1980 | Mueller et al. |
| 4,879,659 | A | * | 11/1989 | Bowlin et al. ................. 700/167 |
| 4,879,752 | A | * | 11/1989 | Aune et al. .................... 382/141 |
| 4,926,350 | A | | 5/1990 | Bechtel et al. |
| 5,097,881 | A | | 3/1992 | Mack |
| 5,135,597 | A | | 8/1992 | Barker |
| 6,293,152 | B1 | | 9/2001 | Stanish et al. |
| 6,305,224 | B1 | | 10/2001 | Stanish et al. |
| 6,308,571 | B1 | | 10/2001 | Stanish et al. |
| 6,358,352 | B1 | | 3/2002 | Schmidt |

(Continued)

FOREIGN PATENT DOCUMENTS

| CA | 2406851 | 4/2003 |
| CA | 2407156 | 5/2003 |
| CA | 2581427 | 9/2007 |

OTHER PUBLICATIONS

McMillin, Charles, et al., ALPS, A potential new automates lumber processsing system, Jan. 1984, Forest Products Journal, vol. 34, No. 1.

*Primary Examiner* — Shelley Self
*Assistant Examiner* — Matthew G Katcoff
(74) *Attorney, Agent, or Firm* — Christensen O'Connor Johnson Kindness PLLC

(57) ABSTRACT

In some embodiments, the disclosure includes method for optimizing lumber derived from a log. The method may include the steps of debarking the log and cutting the log to provide a plurality of boards. The plurality of boards are then scanned to determine knot properties and/or warp stability for each of the plurality of boards and a lumber upgrade process is selected based on the knot properties and/or warp stability. Finally, one or more of the plurality of boards are planed after being subjected to the lumber upgrade process.

3 Claims, 2 Drawing Sheets

(56) References Cited

U.S. PATENT DOCUMENTS

| | | |
|---|---|---|
| 6,690,990 B1 * | 2/2004 | Caron et al. ............... 700/171 |
| 6,705,363 B2 | 3/2004 | McGehee et al. |
| 6,892,614 B2 | 5/2005 | Olsen |
| 6,901,352 B2 | 5/2005 | Woods et al. |
| 7,043,990 B2 | 5/2006 | Wang et al. |
| 2003/0178586 A1 | 9/2003 | Hubert et al. |
| 2005/0045270 A1 * | 3/2005 | Brunet ............... 156/254 |
| 2005/0262977 A1 | 12/2005 | Wilkerson et al. |

* cited by examiner

METHOD FOR OPTIMIZING LUMBER DERIVED FROM A LOG

CROSS-REFERENCE TO RELATED APPLICATIONS

This application is a divisional of and claims the benefit of priority under 35 U.S.C. §120 from U.S. patent application Ser. No. 11/379,515, filed on Apr. 20, 2006, and titled "Method for Optimizing Lumber," the contents of which are incorporated herein by reference.

TECHNICAL FIELD

The present disclosure is directed generally to a method for optimizing lumber by examining boards prior to the planing process

BACKGROUND

Process steps for creating lumber are generally known. In a first step, tree length logs may be delivered to a saw mill. While at the saw mill, the logs may be scanned, optimized, and/or bucked to create shorter blocks or segments. The logs are also scanned for shape and sawn into lumber. The resultant boards may be sorted and scanned for wane. After further trimming, based on wane, the boards are sorted by dimensions, moisture content, and/or wane grade. The boards may then be kiln dried. Next, the boards may be planed to a desired size and finish. The boards may then be split, tested for stress rating, and/or checked for moisture content. The boards are then graded, stamped according to their grade, and eventually packaged for shipping to a customer. It is desirable to optimize the lumber derived from a log. Accordingly, a need exists for a method for examining logs and/or boards prior to the planing process or after the planing process to further optimize the lumber derived from the logs/boards.

SUMMARY

The following summary is provided for the benefit of the reader only and is not intended to limit in any way the invention as set forth by the claims. The present disclosure is directed generally towards a method for optimizing lumber by examining boards prior to the planing process.

In some embodiments, the disclosure includes method for optimizing lumber derived from a log. The method may include the steps of debarking the log and cutting the log to provide a plurality of boards. The plurality of boards are then scanned to determine knot properties for each of the plurality of boards and a lumber upgrade process is selected based on the knot properties. Finally, one or more of the plurality of boards are planed after being subjected to the lumber upgrade process.

In other embodiments, the disclosure includes another method for optimizing lumber derived from a log. The method may include the steps of debarking the log and cutting the log to provide a plurality of boards. The plurality of boards are then scanned to determine a first warp stability for each of the plurality of boards and the boards are sorted based on the first warp stability. The sorted boards are then scanned to determine a second warp stability for each of the plurality of boards. A lumber upgrade process is the selected for each of the boards based on the second warp stability. Finally, one or more of the plurality of boards are planed after being subjected to the lumber upgrade process.

BRIEF DESCRIPTION OF THE DRAWINGS

The present disclosure is better understood by reading the following description of non-limitative embodiments with reference to the attached drawings wherein like parts of each of the figures are identified by the same reference characters, and are briefly described as follows.

DETAILED DESCRIPTION

The present disclosure describes a method for optimizing lumber by examining boards prior to the planing process. Certain specific details are set forth in the following description and FIGS. 1 and 2 to provide a thorough understanding of various embodiments of the disclosure. Well-known structures, systems, and methods often associated with such systems have not been shown or described in detail to avoid unnecessarily obscuring the description of various embodiments of the disclosure. In addition, those of ordinary skill in the relevant art will understand that additional embodiments of the disclosure may be practiced without several of the details described below.

In an embodiment, boards cut from a log are examined for warp stability and/or knots. This occurs prior to the planing process and/or after planing and before grading and grade stamping. Based on the examination for warp stability and/or knots, the boards can be sent to a lumber upgrade process, such as for example, re-drying, edging, splitting, trimming, chopping, chipping, or the like. Accordingly, the method of the present invention enables more efficient allocation of lumber towards manufacturing needs.

Figure 1:
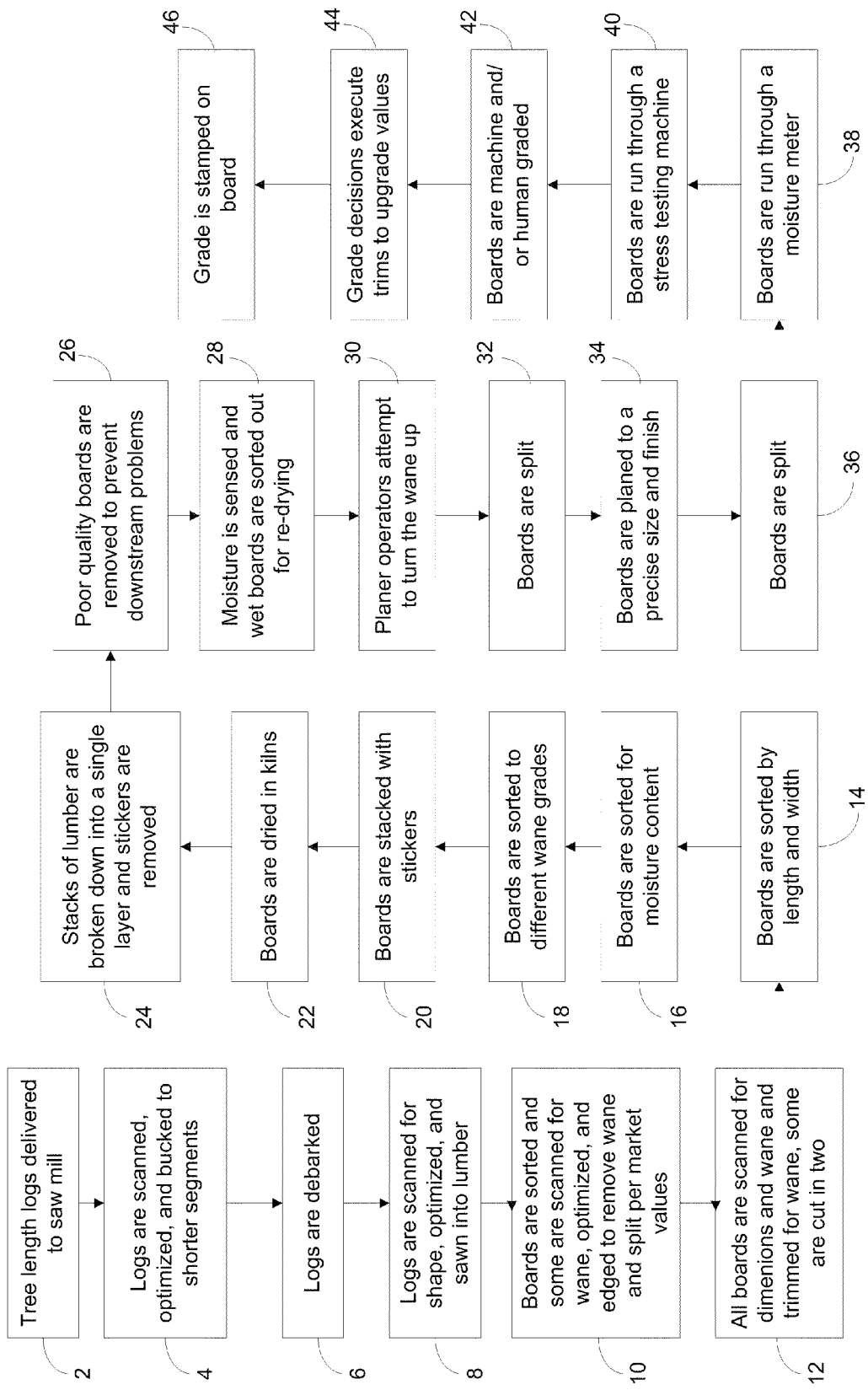
FIG. 1 is a flow chart of the various steps by which lumber is derived from a log according to known methods.

FIG. 1 is a flow chart of the generally known processes by which lumber is derived from a log. In a first step, tree length logs may be delivered to a saw mill, as shown at step 2. While at the saw mill, the logs may be scanned, optimized, and/or bucked to create shorter blocks or segments, as shown at step 4. The logs may then be debarked, as shown at step 6. The logs are also scanned for shape, optimized and sawn into lumber, as shown at step 8. The resultant boards may be sorted and scanned for wane; they may also be optimized, edged to remove wane, or split according to market values, as shown at step 10. As shown at step 12, the boards may be scanned for dimensions and wane, and further trimmed for wane. Some of these boards may be cut into two pieces. As shown at step 14, the boards are sorted by dimensions. In some cases, the boards may also be sorted for moisture content, as shown at step 16; and/or they may be sorted by wane grade, as shown at step 18. Next, the boards are stacked with stickers, as shown at step 20. The boards may then be kiln dried, as shown at step 22. The available methods and equipment for carrying out the functions described above are well known by those skilled in the art. Next, the boards may be sent to a planer mill. Typical equipment and processes used in a planer mill are known by those skilled in the art. While there, the stacks of lumber are broken down into a single layer and the stickers are removed, as shown at step 24. Poor quality boards are removed to prevent downstream problems, as shown at step 26. In some cases, a mill will measure moisture content of the lumber, and wet boards are sorted out for re-drying, as shown at step 28. In some embodiments, a planer operator will attempt to position a board to turn wane in an upward direction to improve grade value, as shown at step 30. In some mills, the boards are split, as shown at step 32. The boards are then planed to a desired size and finish, as shown at step 34. The boards may then be split as shown at step 36. In an embodiment, the boards are checked for moisture content, as shown at step 38. In another embodiment, the boards are tested to provide a stress rating, as shown at step 40. This may occur via, for example, a stress grading machine, such as a Linear High Grading machine, or other devices, such as a Continuous Lumber Tester. The boards are then graded, as shown at step 42. This may be performed by machine and/or human grading. Grade decisions execute trims to increase the board's grade, as shown at step 44. The boards are then stamped according to their grade, as shown at step 46, and eventually packaged for shipping to a customer.

Figure 2:
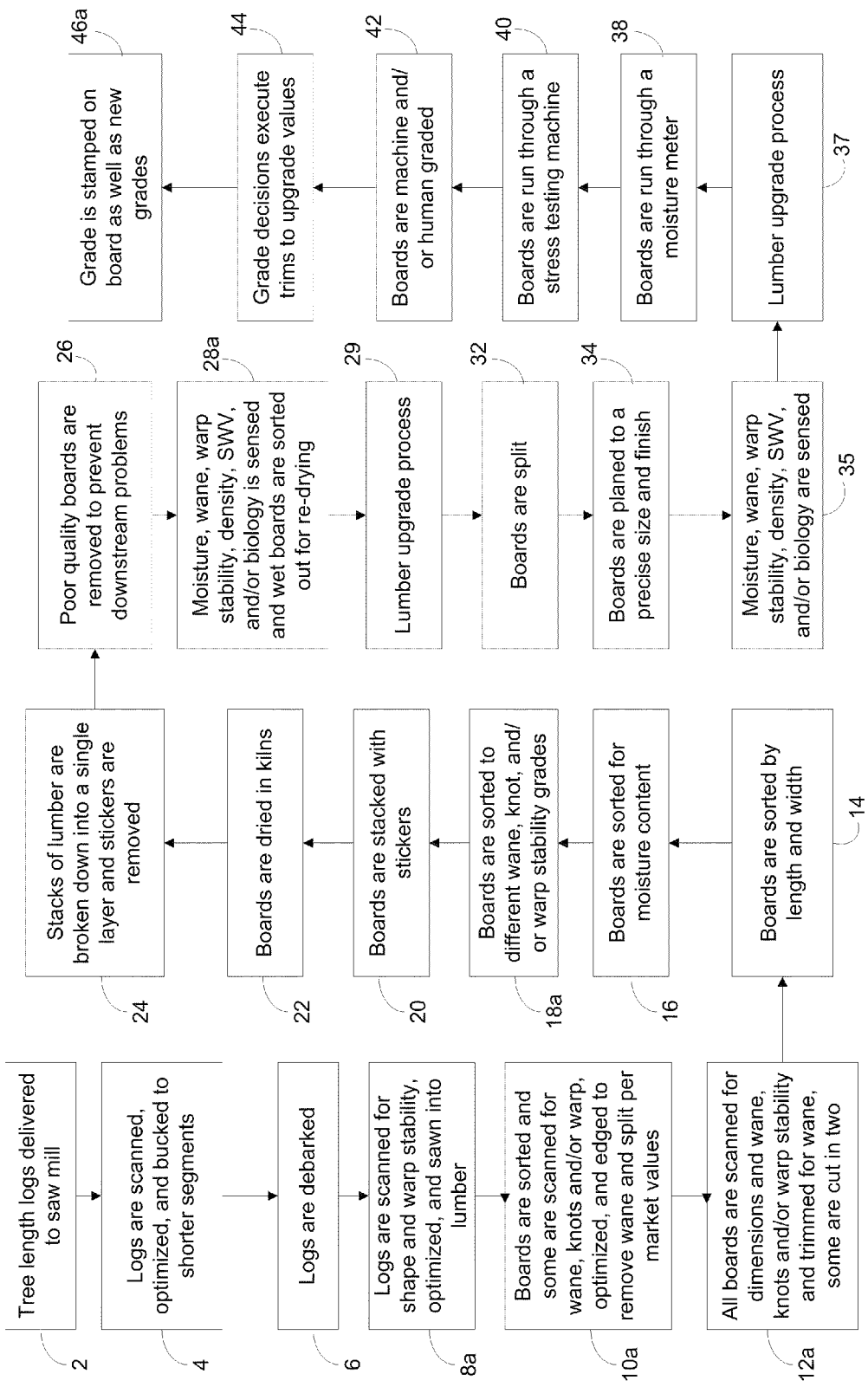
FIG. 2 is a flow chart of the various steps by which lumber is derived from a log in embodiments of the present disclosure.

FIG. 2 illustrates a flow chart comprising process steps of the present invention. Many of the steps illustrated in FIG. 1 present in FIG. 2, and are numbered identically for convenience and better understanding of embodiments of the disclosure. As seen by the figure, steps 2, 4 and 6 may be similar to known processes. Step 8a may differ from step 8 in that the logs may be scanned or otherwise examined for warp stability (potential methods for which will be discussed below). Likewise, step 10a may differ from step 10 in that boards sawn from logs may be scanned or otherwise examined for knots and/or warp stability. These boards may also be optimized and/or edged to remove wane and/or may be split per market values. Step 12a differs from step 12 in that the boards that are trimmed for wane, or cut in two, are scanned or otherwise examined for knots and/or warp stability. Step 18a differs from step 18 in that the boards are sorted according to knot properties and/or warp stability in addition to wane grades. At step 28a boards may be examined for wane, warp stability, density, stress wave velocity, and/or biology in addition to moisture measurement. At step 29, the boards may be sent to the lumber upgrade process based on the examined properties in step 28a. These upgrade processes may be, for example, re-drying, edging, splitting, trimming, chopping, chipping, or the like. The intent of this scanning and preprocessing is to sort boards towards the appropriate manufacturing process and/or to upgrade a board for the planing process. For example, the method may involve upgrading wet boards by microwave redrying; passing those wide boards that have the greatest value as wides through the lumber process; splitting those wide boards to become narrow boards if the board quality allows more value in a narrow boards; edging those boards that could be upgraded by removing wane; or trimming or chopping a board before planing to get more value for the rough trim blocks than planed trim blocks. The warp stability and/or knot property examination may allow additional grades to be assigned to the boards respective of these characteristics, as shown at step 46a; prior to packaging and transport to a customer.

In an embodiment, the boards may be examined after being planed, as shown at step 35. More specifically, the examination may be for moisture, wane, warp, stability, density, stress wave velocity, biology, or the like. The boards may then be sent for an upgrade process, similar to those described above, as shown at step 37. In this embodiment, it is contemplated that the boards could be examined both before and after the planing process. In an embodiment, part of the examination of the board may be done before the planing process and part of the examining process may be done afterwards. In this embodiment, it is contemplated that only certain properties are examined prior to planing, and other properties are examined after planing. In other embodiments, the boards may be examined either before or after the planing process. Further, logs may or may not be examined for warp stability and/or knot properties prior to being sawn for lumber.

The methods for determining warp stability or any of the other properties mentioned above may involve the use of single and/or multiple sensor group systems to provide qualitative and/or quantitative estimates. It has been discovered that estimates of warp/dimensional stability can be much improved when an assortment of measurements are used together, where each measurement contributes information relating to one or more variables. The measurements may be taken at one or more sections of the wood product (i.e., log or board), which may differ in size given a particular embodiment. The properties observed at the one or more sections may allow a qualitative and/or quantitative estimate of dimensional stability of a region of interest. In a first embodiment, the region of interest may be a coupon or other portion of the wood product. In another embodiment, the region of interest may overlap with one or more sections of the wood product. In another embodiment, the region of interest may be the entire wood product. In yet another embodiment, the region of interest may be the same as the one or more sections detected by the sensor group(s). In another embodiment, the region of interest does not have an overlap with the one or more sections. The dimensional stability assessed may be cup, crook, bow, twist, length stability, thickness stability, width stability, or any combination of these.

In an embodiment of the present invention, a classification algorithm may be created to classify a wood product into one of a plurality of groups or categories. The groups may be based on qualitative or quantitative characteristics. For example, in an embodiment, the categories may be different grades. Warp classification of wood products, such as boards may require inputs from one or more sensor groups detecting properties of the boards. The sensor groups may be a part of those systems previously mentioned for analyzing a wood product. The technologies for these systems are known by those skilled in the art. For example, the sensor groups may obtain moisture content measurement, electrical property measurement, structural property measurement, acousto-ultrasonic property measurement, light scatter (tracheid-effect) measurement, grain angle measurement, shape measurement, color measurement, spectral measurement and/or defect maps. Structural property measurement may measure modulus of elasticity, density, specific gravity, strength, or a combination of these. Acousto-ultrasonic property measurement measures may measure velocity and/or damping. The spectral measurement may be characterized by absorption or reflectance values over a wavelength spectrum ranging from ultraviolet through near infrared.

Using this approach, the prediction model or algorithm of embodiments of the disclosure may use inputs of many different resolution scales. Some examples are board average MOE, moisture content measured across the width of the board in one foot increments along the length of the board, spectroscopy data collected every inch, or laser data collected every 1/a inch. The inputs are functions of the sensor signals and may be either quantitative or qualitative. For example, an input could be the estimated moisture content for each 12 inch lineal section of a piece of lumber, as estimated by a moisture meter. Another example is an indicator for the presence or absence of a knot in a 12 inch by 1 inch section of wood, based on a color image. Inputs may be direct sensor measurements, preprocessed signals, combined signals from several sensors or predicted measures from other sensors. Signal pre-processing may include, but is not limited to, such steps as filtering, smoothing, derivative calculations, power spectrum calculations, Fourier transforms, etc., as is well known in the art. Predicted measurements from other sensors may include, but are not limited to, shrinkage-coefficients predicted from sensors which measure the light scattering and light absorption properties of wood and used as inputs to a partial least squares, or "PLS", prediction model.

The prediction algorithm(s) or model(s) based on the set of inputs can be derived using many techniques which include, but are not limited to, regression trees, classification trees, linear discriminant analysis, quadratic discriminant analysis, logistic regression, Partial Least Squares or other supervised learning techniques such as neural networks. There are many forms of equations or algorithms that could be used. These algorithms can be developed to classify boards into 2 or more groups. For example, boards might be classified into four grades (#1 grade, #2 grade, #3 grade, #4 grade) or into two classifications like warp stable and warp unstable, or into three categories like crook less than 0.25 inches, crook between 0.25 and 0.5 inches, crook greater than 0.5 inches. Typically, the parameters in the models or algorithms are derived from a training-set of data and the performance is tested on a testing-set of data before being used in production, although other approaches exist.

Various embodiments are contemplated involving the use of sensor groups and algorithms. In a first embodiment, a single sensor group may provide inputs to a classification algorithm which classifies wood products into one of a plurality of groups or categories, such as grades, for example.

In a second embodiment, a single sensor group may provide inputs to a classification algorithm as in the previous example. However, in this embodiment, a second algorithm may be selected after classifying the wood product. This second algorithm may be selected from a plurality of algorithms which are used to assess the dimensional stability in a quantitative manner.

In a third embodiment, two or more sensor groups may provide two or more inputs to a classification algorithm to classify wood products into one of a plurality of categories.

In a fourth embodiment, two or more sensor groups may provide two or more inputs to an algorithm for providing a quantitative assessment of dimensional stability of wood products.

In a fifth embodiment, two or more sensor groups may provide two or more inputs to a classification algorithm to classify wood products into one of a plurality of categories. Next, a second algorithm may be selected after classifying the wood product. This second algorithm may be selected from a plurality of algorithms which are used to assess the dimensional stability in a quantitative manner. Other methods for determining warp stability, wane, moisture, knot properties, or the like for a log or board are contemplated, including those described in U.S. Pat. Nos. 6,308,571; 6,305,224; and 6,293,152 to Stanish et al., or any other known methods currently used at mill sites. These methods could be implemented into the process steps described above.

While the embodiments of the disclosure have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

The invention claimed is:

1. A method for optimizing lumber derived from a log, the method comprising the steps of:
   debarking the log;
   cutting the log to provide a plurality of boards;
   scanning the plurality of boards to determine a first warp stability for each of the plurality of boards;
   sorting the plurality of boards based on the first warp stability;
   scanning the plurality of boards to determine a second warp stability for each of the plurality of boards;
   selecting a lumber upgrade process for each of the plurality of boards based on the second warp stability;
   processing each of the plurality of boards based on the selected lumber process; and
   planing one or more of the plurality of boards after the board is subjected to the lumber upgrade process.

2. The method of claim 1 wherein the lumber upgrade process is edging of the board.

3. The method of claim 1 wherein the lumber upgrade process selected is also based on knot properties.

* * * * *